United States Patent
Houston et al.

(10) Patent No.: US 9,649,186 B2
(45) Date of Patent: May 16, 2017

(54) TUBULAR CONDUIT

(71) Applicant: Vascular Flow Technologies Limited, Dundee (GB)

(72) Inventors: John Graeme Houston, Perth (GB); Peter Arno Stonebridge, Perth (GB)

(73) Assignee: Vascular Flow Technologies Limited, Dundee (GB)

( * ) Notice: Subject to any disclaimer, the term of this patent is extended or adjusted under 35 U.S.C. 154(b) by 36 days.

(21) Appl. No.: 13/919,812

(22) Filed: Jun. 17, 2013

(65) Prior Publication Data

US 2013/0282108 A1  Oct. 24, 2013

Related U.S. Application Data

(63) Continuation of application No. 13/509,628, filed as application No. PCT/GB2010/002121 on Nov. 17, 2010, now abandoned.

(30) Foreign Application Priority Data

Nov. 17, 2009 (GB) .................................... 0920115.3

(51) Int. Cl.
*A61F 2/06* (2013.01)
*B29C 45/14* (2006.01)
(Continued)

(52) U.S. Cl.
CPC ............ *A61F 2/06* (2013.01); *B29C 45/1418* (2013.01); *B29C 45/14622* (2013.01); *A61F 2/07* (2013.01);
(Continued)

(58) Field of Classification Search
CPC .................. A61F 2/07; A61F 2002/072; A61F 2002/075; A61F 2002/077
(Continued)

(56) References Cited

U.S. PATENT DOCUMENTS 6,514,284 B1  2/2003  Cheng
2003/0120257 A1  6/2003  Houston et al.
(Continued)

FOREIGN PATENT DOCUMENTS

CN  101065078 A  10/2007
CN  101384228 A  3/2009
(Continued)

OTHER PUBLICATIONS

Adam Tucker, "GB Patent Application No. GB 0920115.3 Search Report", Mar. 8, 2010, Publisher: GB IPO, Published in: GB.
(Continued)

*Primary Examiner* — Katrina Stransky
*Assistant Examiner* — Daniel Bissing
(74) *Attorney, Agent, or Firm* — Kaplan Breyer Schwarz & Ottesen, LLP (57) ABSTRACT

A tubular conduit comprising: a tubular portion made from a flexible material. There is an external helical formation extending around the exterior of, and parallel to the axis of, the tubular portion and defining a first region of the tubular portion. The external helical formation is for supporting the tubular portion. There is also an internal helical formation, protruding inwardly of the interior of the tubular portion and extending parallel to the axis of the tubular portion and defining a second region of the tubular portion. The internal helical formation is for imparting helical flow on fluid passing through the tubular portion. The first region does not extend throughout the second region.

17 Claims, 3 Drawing Sheets

(51) Int. Cl.
    *A61F 2/07* (2013.01)
    *B29L 23/00* (2006.01)
    *B29K 627/18* (2006.01)

(52) U.S. Cl.
    CPC ... *A61F 2002/068* (2013.01); *A61F 2002/072* (2013.01); *B29K 2627/18* (2013.01); *B29L 2023/007* (2013.01)

(58) Field of Classification Search
    USPC ..................................... 623/1.13, 1.14, 1.22
    See application file for complete search history.

(56) References Cited

U.S. PATENT DOCUMENTS

2003/0204245 A1* 10/2003 Brightbill ............... A61F 2/915
    623/1.16
2004/0147929 A1* 7/2004 Biedermann ...... A61B 17/7001
    606/266
2006/0265051 A1 11/2006 Caro et al.

FOREIGN PATENT DOCUMENTS

| | | | | |
|---|---|---|---|---|
| EP | 1799152 | B1 | 9/2004 | |
| EP | 1637090 | A2 | 3/2006 | |
| EP | 1759667 | A1 | 3/2007 | |
| EP | 1948082 | A2 | 7/2008 | |
| EP | 1605868 | B1 | 12/2008 | |
| GB | 2379996 | A | 3/2003 | |
| GB | 2429650 | A * | 3/2007 | ............... A61F 2/06 |
| JP | H04253856 | A | 9/1992 | |
| WO | 8303349 | A1 | 10/1983 | |
| WO | 0038591 | A2 | 7/2000 | |
| WO | 0162185 | A1 | 8/2001 | |
| WO | 0189419 | A1 | 11/2001 | |
| WO | 2004047908 | A2 | 6/2004 | |
| WO | 2005092240 | A1 | 10/2005 | |

OTHER PUBLICATIONS

Serra I Verdaguer, J., "PCT Application No. PCT/GB2010/002121 International Search Report Apr. 19, 2011", , Publisher: PCT, Published in: PCT.

Athina Nickitas-Etienne, "International Patent Application No. PCT/GB2010/002121 International Preliminary Report on Patentability", May 31, 2012, Publisher: PCT, Published in: GB.

* cited by examiner

TUBULAR CONDUIT

CROSS-REFERENCE TO RELATED APPLICATIONS

U.S. patent application Ser. No. 13/509,628, with a 371 entry date of May 14, 2012, is incorporated herein by reference.

FIELD OF THE INVENTION

The present invention relates to a tubular conduit and to methods of making a tubular conduit.

BACKGROUND OF THE INVENTION

It is known in the art to provide vascular grafts as artificial vascular prostheses to be implanted in individuals with diseased blood vessels. For example, if an individual is suffering from atherosclerosis then a section of blood vessel may be replaced or bypassed with a vascular graft.

The problem with such vascular grafts is that they have a tendency to cause turbulence in the flow of the blood that they carry, particularly at the join between the vascular graft and the blood vessel at either end. This can result in plaque or tissue formation, reduced flow capacity and thrombosis, or occlusion in the blood vessel.

WO-A-00138591 discloses a vascular graft in which a tubular graft is provided with four equally spaced ridges on the interior of the graft. Each ridge is in the form of an axially extending helix. The ridges induce helical flow on the blood passing through the vascular graft. The provision of helical blood flow reduces the turbulence of the blood in the vascular graft which, in turn, reduces the likelihood of plaque formation, reduced flow capacity, thromboses or occlusion.

A problem with vascular grafts, in general, whether or not they have an internal helical formation is that while vascular grafts are usually flexible, they do not exactly replicate the physical properties of the blood vessel that they replace. Normally, the vascular graft will follow a smooth curve when it is bent. However, if it is bent excessively, either during implantation or due to the bending movement in vivo (for example, bending that occurs at a joint) then there is a risk that, instead of forming a smooth curve the graft will form a kink, effectively blocking the cross-section of the vascular graft. If a kink occurs while the vascular graft is implanted then this can be very dangerous as blood flow is significantly reduced or occluded.

One solution to this problem is disclosed in WO-A-20051092240. A vascular graft is disclosed which comprises an internal helical formation having a helix angle in the range of between 8° and 20° and which imparts helical flow on blood passing through the graft and an external helical formation, which has a helix angle greater than 50°, which is for supporting the vascular graft and preventing kinking of the graft. While this vascular graft works well and has been successfully implanted into patients, there are certain features of its construction which are sub-optimal. In particular, it has been found that the presence of both the internal helical formation and the external helical formation on the vascular graft can result in the graft being more stiff than is desired by surgeons implanting the graft. This is particularly so where the graft is for implantation from the groin of a patient to just above the knee of the patient (i.e. an above knee femoropopliteal bypass graft) as space for the implantation procedure is particularly limited for a surgeon at these sites.

The construction of the vascular graft in WO-A-2005/092240 is such that the internal helical formation is reinforced by an external deformation helix which sits in a helical groove in the exterior of the tubular graft. Where the external helical formation and the deformation helix intersect, they are fused together. One potential disadvantage with this arrangement is that if the external helical formation is damaged, for example during inadvertent mishandling during implantation, it could dislodge the deformation helix and thereby weaken the structural integrity of the internal helical formation.

The present invention seeks to alleviate one or more of the above problems and has arisen from the realisation that a better balance between the stiffness and flexibility of a vascular graft can be achieved by omitting the external helical formation from the vascular grafts in regions where the internal helical formation is present, thereby reducing the stiffness of the vascular graft without unduly risking kinking of the graft. While such a vascular graft is useful at all sites of implantation, it is particularly useful at implantation sites at anatomical locations, either where little or no bending of the graft is required (e.g. for an above knee femoropopliteal bypass graft), or where bending is normal, i.e. where the graft route is across a joint, for example across the knee in a below knee femoropopliteal bypass. Such grafts may also be beneficial for implantation at other grafts sites, such as, but not exclusively, vascular dialysis access grafts across the elbow, axillofemoral grafts and aortobifemoral grafts across the hip.

SUMMARY OF THE OF INVENTION

According to a first aspect of the present invention, there is provided a tubular conduit comprising:

a tubular portion made from a flexible material;

an external helical formation extending around the exterior of, and parallel to the axis of, the tubular portion and defining a first region of the tubular portion, the external helical formation being for supporting the tubular portion; and an internal helical formation, protruding inwardly of the interior of the tubular portion and extending parallel to the axis of the tubular portion and defining a second region of the tubular portion, the internal helical formation being for imparting helical flow on fluid passing through the tubular portion, wherein the first region does not extend throughout the second region.

Preferably the tubular conduit is a vascular graft and the fluid is blood.

Conveniently the helix angle of the external helical formation is different from the helix angle of the internal helical formation.

Preferably the helix angle of the external helical formation is greater than the helix angle of the internal helical formation.

Advantageously, the helix angle of the external helical formation is greater than 50°, preferably between 65° and 80°.

Preferably, the helix angle of the internal helical formation is between 8° and 20°, more preferably between 12° and 18°, more preferably between 12° and 14°.

Preferably, the first and second regions overlap.

Conveniently, the overlap between the first and second regions is of a length of between 1 and 5 revolutions of the external helical formation, preferably between 2 and 5 revolutions thereof and most preferably between one and half and two and half revolutions (e.g. two revolutions) thereof. Alternatively, the overlap between the first and second regions is less than 50 or 80% of one revolution of the internal helical formation.

Preferably, the first region does not extend throughout all parts of the second region that extend along sections of the tubular portion having a complete perimeter.

Advantageously, the internal helical formation comprises a section of the tubular portion deformed by an axially extending deformation helix.

Preferably, the external helical formation is fused with the deformation helix where the external helical formation and the deformation helix intersect.

Advantageously, the deformation helix comprises polyurethane.

Preferably, the tubular portion comprises ePTFE.

Conveniently, the deformation helix is sintered to the tubular portion.

Advantageously, the internal helical formation consists of between 80% and 120% of a single revolution.

Preferably, the internal helical formation terminates at one end of the tubular portion.

Conveniently, said one end of the tubular portion tapers from an inner base to an outer tip and said one end of the tubular portion defines a substantially elliptical orifice.

Advantageously, the internal helical formation terminates at the orifice defined by said one end of the tubular portion at a point along an arc within 90° either side of the inner base.

Preferably, the internal helical formation terminates, at its other end, at a point short of the other end of the tubular portion. It is particularly preferred that the internal helical formation terminates at a point short of any part of the other end of the tubular portion.

For example, the internal helical formation extends for less than 50%, less than 25% or less than 10% of the entire length of the tubular portion.

According to a second aspect of the present invention, there is provided a method of making a tubular conduit comprising the steps of:
(i) providing a flexible tubular portion having a pre-formed helical formation extending axially along the exterior of a region of the tubular portion;
(ii) flowing a moulding liquid in a first axially extending, helical form around the exterior of the tubular portion, the first helical form having the same helix angle and phase as the pre-formed helical formation and extending beyond one end of the pre-formed helical formation such that a contiguous external helical formation is formed; and
(iii) solidifying the moulding liquid.

Conveniently, step (ii) further comprises the step of flowing the moulding liquid in a second axially extending helical form around the exterior of the tubular portion.

Preferably the first and second helical forms each has a different helix angle.

Advantageously, the helix angle of the first helical form is greater than the helix angle of the second helical form.

Advantageously, the helix angle of the first helical form is greater than 50°, preferably between 65° and 80°.

Conveniently, the helix angle of the second helical form is between 8° and 20°, preferably between 12° and 18°, more preferably between 12° and 14°.

Advantageously, step (ii) comprises: (a) deforming the tubular portion so as to provide an internal helical protrusion on the inside of the tubular portion and a corresponding external helical groove; and (b) flowing the moulding liquid into the external helical groove to form the second helical form.

Conveniently, the contiguous external helical formation defines a first region of the tubular portion and the second helical form defines a second region of the tubular portion and the first region does not extend throughout the second region.

Advantageously, the first region and the second region overlap.

Preferably, the first region does not extend throughout all parts of the second region that extend along sections of the tubular portion having a complete perimeter.

Conveniently, the overlap between the first and second regions is of a length of between 1 and 5 revolutions of the external helical formation, preferably between 2 and 5 revolutions thereof and most preferably between one and half and two and half revolutions (e.g. two revolutions) thereof. Alternatively, the overlap between the first and second regions is less than 50 or 80% of one revolution of the internal helical formation.

Preferably, step (ii) comprises locating the tubular portion over a mandrel; and encasing the tubular portion within a mould such that the tubular portion is sandwiched between the mandrel and the mould.

Advantageously, the mandrel has an axially extending helical channel on its surface and wherein step (a) further comprises the step of introducing the moulding liquid between the tubular portion and the mould such that the moulding liquid deforms the tubular portion by pressing the tubular portion into the helical channel on the mandrel to provide the internal helical protrusion.

Conveniently, the method further comprises, between the steps of locating the tubular portion over the mandrel and encasing the tubular portion within the mould, the step of pushing the tubular portion at least partially into the helical channel of the mandrel.

Advantageously, the step of introducing the moulding liquid comprises injecting the moulding liquid into the mould above the helical channel in the mandrel.

Conveniently, the mould has an axially extending helical channel about its inside surface and step (b) further comprises the step of introducing the moulding liquid between the tubular portion and the mould such that the moulding liquid flows into the helical channel in the mould.

Preferably, the tubular portion is aligned within the mould so that the pre-formed helical formation is in the same phase as, and overlaps with or abuts, the axially extending helical channel about the inside surface of the mould. The helix angle of the axially extending helical channel and the preformed helical formation are the same.

Advantageously, one end of the tubular portion tapers from an inner base to an outer tip such that said one end defines an orifice which is substantially elliptical.

Conveniently, the tubular portion is aligned on the mandrel such that the axially extending helical channel on the surface of the mandrel terminates at the orifice defined by said one end of the tubular portion, at a point along an arc within 90° either side of the inner base.

Advantageously, the method further comprises between steps (ii) and (iii), the step of sintering the moulding liquid onto the flexible material or the tubular portion.

Conveniently, step (ii) is carried out between 600 and 800 kPa and between 170° C. and 210° C., preferably, at 689 kPa and 190° C.

Preferably, the moulding liquid comprises polyurethane.

Conveniently, the flexible material comprises ePTFE.

The terms "helix" and "helical" are used herein to cover the mathematical definition of helix and helical and any combination of mathematical definitions of helical and spiral.

The term "helix angle" is used herein, in relation to a tubular conduit, to refer to the angle between a helix on the conduit and the longitudinal axis of the conduit.

In this specification, where a helical formation is said to extend parallel to the axis of a tubular portion this means that the axis of the helical formation is parallel to the axis of the tubular portion.

DETAILED DESCRIPTION

Figures 1, 2:
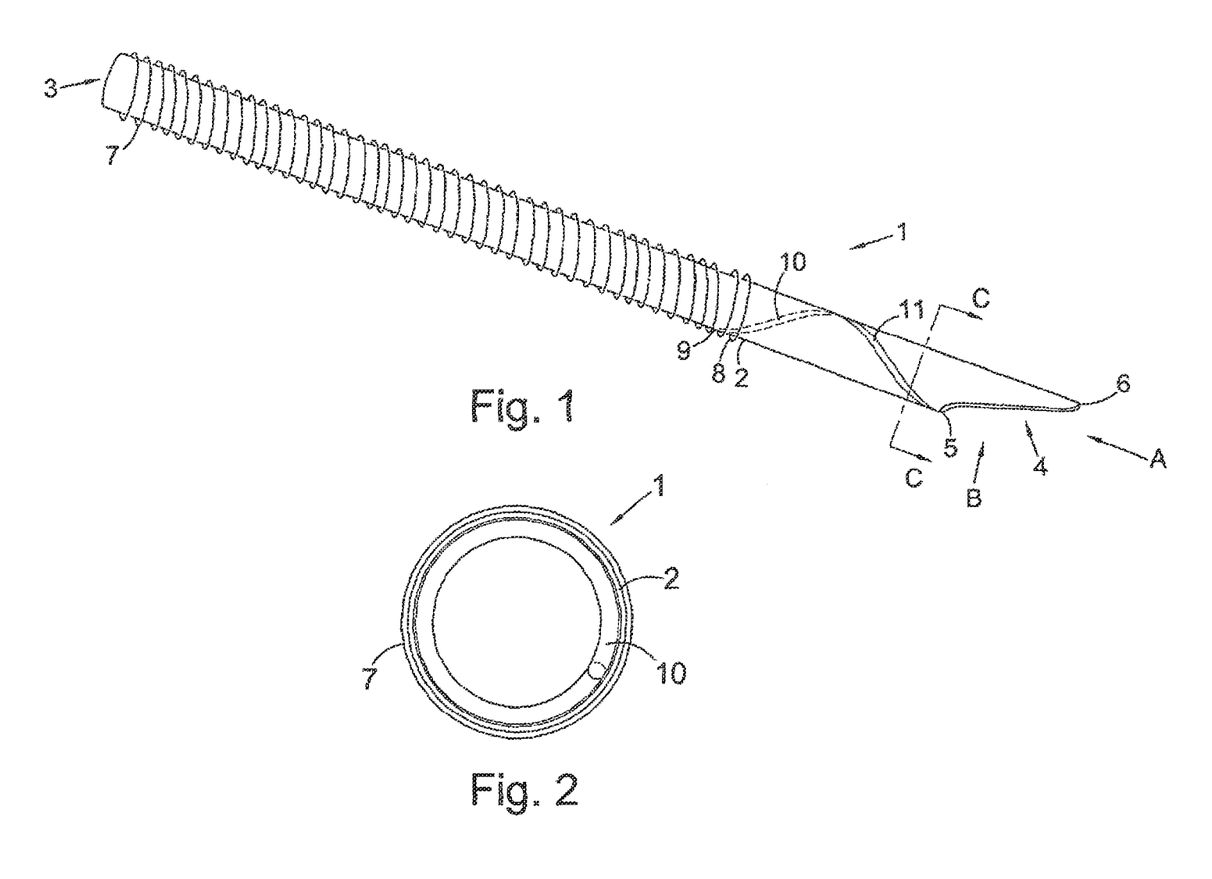
FIG. 1 is a perspective view of a vascular graft in accordance with one embodiment of the present invention.
FIG. 2 is a view along the arrow A of the vascular graft shown in FIG. 1.
Figure 3:
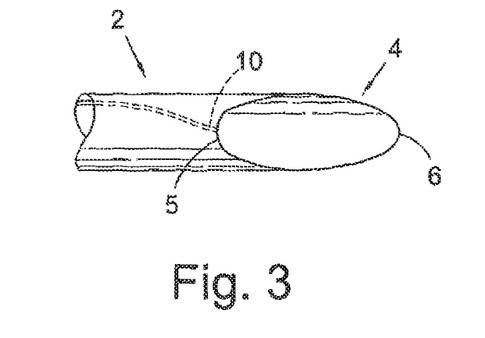
FIG. 3 is a view along the arrow B of the vascular graft shown in FIG. 1.

Referring to FIG. 1, a vascular graft 1 in accordance with one embodiment of the present invention is shown. The vascular graft 1 comprises a flexible tubular portion 2 having a generally circular cross-section and made from expanded polytetrafluoroethylene (ePTFE). The tubular portion 2 has first and second ends 3, 4. The tubular portion 2 is hollow and thus the first and second ends, 3, 4 define respective first and second orifices which give access to the interior lumen of the tubular portion 2. The first end 3 terminates at right angles to the longitudinal of the tubular portion 2. However, the second end 4 is cut along a line oblique to the longitudinal axis of the tubular graft 2 so that the second end 4 is tapered. More specifically, the second end 4 is cut sinusoidally so that when viewed in the direction of arrow B (see FIG. 3) the second end 4 defines an "egg-shaped" orifice. That is to say, the orifice of the second end 4 is approximately elliptic but has a curved inner base 5 with a relatively large radius of curvature (i.e. a blurt end) and a curved outer tip 6 with a relatively small radius of curvature (i.e. a sharper end).

Extending around the exterior of the tubular portion 2, from the first end 3, and parallel to the longitudinal axis of the tubular portion 2 is an external support helix 7. The external support helix 7 has a helix angle of greater than 50° and preferably between 85° and 80° and is moulded from polyurethane. Thus the external support helix 7 protrudes slightly outwardly from the outer surface of the tubular portion 2. The external support helix 7 extends from the first end 3 of the tubular portion 2 and ends at a termination point 8. Thus the external support helix defines a first region of the tubular portion 2 which extends from the first end 3 of the tubular portion 2 to the termination point 8.

Starting at an initiation point 9 (which is slightly closer to the first end 3 of the tubular portion 2 than is the termination point 8) an internal inducer helix 10 extends along the tubular portion 2. The internal inducer helix 10 is formed by an inward deformation of the tubular portion 2 from its generally circular cross-section. Thus the internal inducer helix 18 protrudes from the inner surface of the remainder of the tubular portion 2 into the lumen of the tubular portion 2. The internal inducer helix 10 extends parallel to the longitudinal axis of the tubular portion 2 and has a helix angle of between 8° and 20° and preferably between 12° and 18°, more preferably between 12° and 14°. Thus the helix angle of the external support helix 7 is different from and indeed greater than the helix angle of the internal inducer helix 10. The internal inducer helix 10 extends along the interior of the tubular portion 2 for one complete revolution and then terminates at the inner base 5 of the second end 4 of the tubular portion 2. It is not essential to the invention that the internal inducer helix 10 terminates precisely at the inner base 5. In some alternative embodiments, the internal inducer helix 10 terminates at the orifice defined by the second end 4 at a point along an arc within 90° either side of the inner base 5 (i.e. closer to the inner base 5 than to the outer tip 6). It is preferred that it terminates within 45° either side of the inner base 5.

Figure 4:
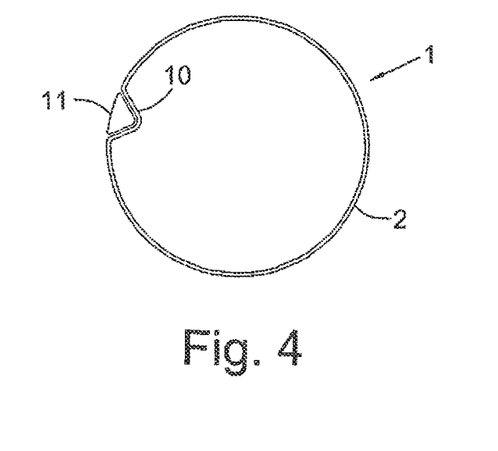
FIG. 4 is a cross-sectional view of the vascular graft of FIG. 1, along the line C-C.

The internal inducer helix 10 has a corresponding external deformation helix 11, which extends along the exterior of the tubular portion 2 and follows the path of the internal inducer helix 10. The external deformation helix 11 is made from polyurethane and lies flush with the outer surface of the tubular portion 2, extending radially inwardly, of the outer perimeter defined by the remainder of the cuter surface of the tubular portion 2 thus reinforcing the structure of the internal inducer helix 10 (see FIG. 4).

The internal inducer helix 10 and the external deformation helix 11 together define a second region of the tubular portion 2 which extends from the initiation point 9 to the inner base 5 at the second end 4 of the tubular portion 2.

The first region and the second region thus overlap slightly between the termination point 8 and the initiation point 9. In particular, the two revolutions of the external support helix 7 which are adjacent to the termination point 8 overlap with the section of the deformation helix 11 adjacent to the initiation point 9. The external support helix 7 and the deformation helix 11 are both made from polyurethane and where the two helices intersect, the external support helix 7 and the deformation helix 11 are fused together. In this way, the deformation helix 11 is anchored in place and the terminal revolutions of the external support helix 7 prevent the deformation helix 11 from lifting out of the tubular portion 2 which could otherwise give rise to a loss of integrity of the internal inducer helix 10. In addition, the second region of the tubular portion 2 is more flexible and less stiff than it would be if the external support helix 7 extended ail the way through the second region. This comparative flexibility makes it easier for a surgeon to implant the vascular graft 1, particularly at relatively inaccessible sites in a patient's human body.

In the above-described embodiment, two revolutions of the external support helix 7 overlap with the deformation helix 11 and the internal inducer helix 10. However, in alternative embodiments, the overlap is between one and five revolutions of the external support helix 7 and in some embodiments there is no overlap (e.g. the external support helix 7 abuts the deformation helix 11 and the internal inducer helix 10). In other embodiments, the overlap between the external support helix 7 and the internal inducer helix 10 is less than 80% or less than 50% of one revolution of the internal inducer helix (less than 6, 8 or 10 cm, in practice).

As explained above, in the embodiment shown in FIG. 1, the second end 4 is tapered and, in some alternative embodiments, the internal inducer helix 10 terminates at the orifice defined by the second end 4 at a point either side of the inner base 5. Thus, in these alternative embodiments, the internal inducer helix 10 extends along sections of the tubular portion 2 that form part of the tapered second end 4 and so do not have a complete perimeter (i.e. a cross-section of the tubular portion 2 perpendicular to the axis of the tubular portion 2 does not form a full circuit at the tapered second end 4).

Nevertheless, it is preferred that, if the first and second regions overlap at all, the first region does not extend all the way along the parts of the second region that extend along sections of the tubular portion 2 having a complete perimeter. That is to say, in addition to the tapered second end 4, there are parts of the second region extending along the main section of the tubular portion 2 along which the first region does not extend. This is preferred because the increased flexibility in the vascular graft 1 is desirable along sections of the tubular portion 2 closer to the axial centre thereof (and thus having a complete perimeter) and not just at the tapered second end 4.

Figure 5:
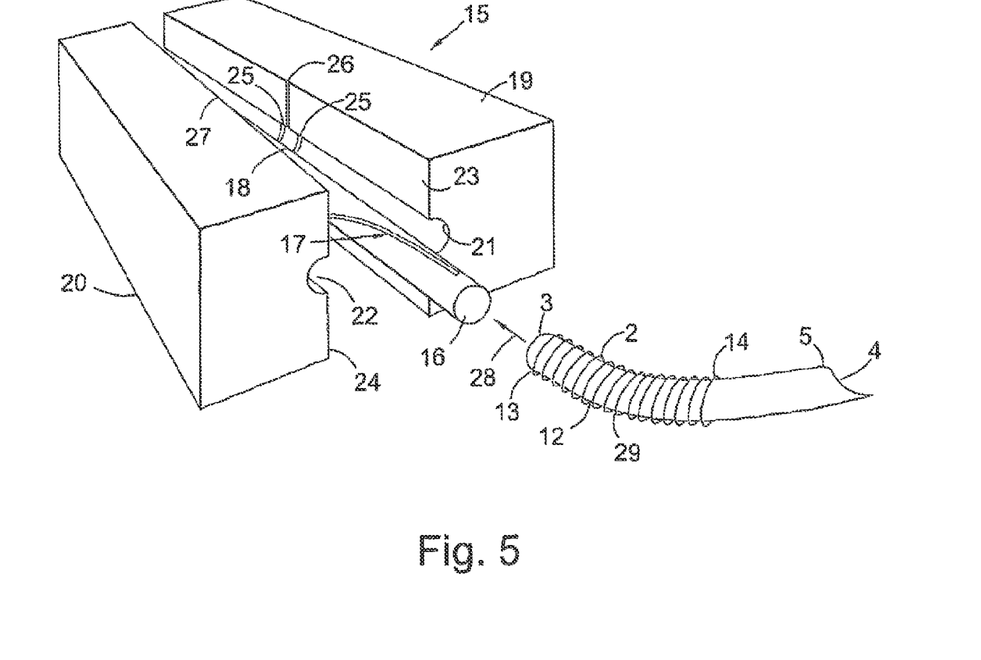
FIG. 5 is a perspective view of a vascular graft prior to a method of the present invention and the mould equipment used in one embodiment of the present invention.

Referring to FIG. 5, a method of producing a vascular graft in accordance with one embodiment of the invention will now be described. A blank vascular graft 12 is provided. The blank vascular graft 12 comprises a flexible tubular portion 13 made from ePTFE and a pre-formed external support helix 29, made from polyurethane. The pre-formed external support helix 29 extends from the first end 3 of the tubular portion to a preformed termination point 14 which is closer to the first end 3 than are the termination point 8 and the initiation point 9 but in all other respects the pre-formed external support helix 29 is identical to the external support helix 7 of the final product shown in FIG. 1. Such blank vascular grafts 12 are available from Vascutek Ltd, Renfrewshire, UK. If necessary, any external support helix which is beyond the preformed termination print 14 is stripped off prior to continuing.

It is to be understood that a range of blank vascular grafts 12 comprising a flexible tubular portion 13 made from ePTFE are commercially available and the present invention is not limited to any particular type or construction. For example, the blank vascular graft by of any type, including but not limited to: standard wall, thinwall, ultrathin, coated or non-coated. Furthermore, the blank vascular graft 12 may or may not be "wrapped", i.e. have an additional layer of ePTFE wrapped around it prior to addition of the pre-formed external support helix 29. As another example, the ePTFE from which the tubular portion 13 is constructed may have any of a range of inter-nodal spacing.

In order to provide the remainder of the external support helix 7 and the deformation helix 11 on the blank vascular graft 12, a mould 15 is provided together with a mandrel 16. The mandrel 16 is an elongate cylinder having an axially extending helical channel 17 in its outer surface. The helical channel 17 has the same helix angle as the internal inducer helix 10. In this embodiment, the length of the mandrel 16 and the helix angle of the helical channel 17 are chosen such that the helical channel 17 forms one complete helical revolution and ends at a mandrel termination point 18.

The mould 15 comprises first and second mould blocks 19, 20. Each mould block 19, 20 is cuboidal and has a semi-circular channel 21, 22 extending in an axial direction along one side 23, 24 of the cuboidal block 19, 20. The semicircular channels 21, 22 are adjacent one another, the two semi-circular channels, 21, 22 together forming a cylindrical bore in which the mandrel 16 can be received with just enough space remaining for the presence of the blank vascular graft 12.

On the inside surface of the semi-circular channels 21, 22 on each of the mould blocks 19, 20 there is provided a pair of arcuate grooves 25 which are arranged such that when the mould blocks 19, 20 are adjacent one another, the arcuate grooves 25 on each of the mould blocks 19, 20 join to form a single helical channel, extending in an axial direction, about the interior of the bore that is formed. The single helical channel consists of two revolutions and has the same helix angle as the external support helix 7. The arcuate grooves 25 are located such that when the mandrel 16 is present in the bore defined by the first and second mould blocks 19, 20, the single helical channel exists around the helical channel 17 adjacent to the mandrel termination point 18.

An injection channel 26, 27 is provided in each of the mould blocks 19, 20 leading from the respective semi-circular channels 21, 22 to the exterior of the mould blocks 19, 20. The injection channels 26, 27 are arranged such that when the mould blocks 19, 20 are adjacent one another, the two injection channels 26, 27 are aligned to form a single injection hole leading from the exterior of the mould 15 to the cylindrical bore formed by the semi-conductor channels 21, 22.

Means are provided (not shown) to lock the two mould blocks 19, 20 together in the configuration whereby the cylindrical bore and the single injection hole are formed. In some embodiments, the means comprise retaining screws.

In order to produce the finished vascular graft 1, the mould 15 is heated. In this embodiment, the mould 15 is heated to 190° C. but the exact temperature used in each embodiment is dependent upon the materials that are used in the process.

The two mould blocks 19, 20 and the mandrel 16 are separated from one another. The blank vascular graft 12 is then fitted onto the mandrel 16 in the direction of the arrow 28 in FIG. 4. The blank vascular graft 12 is aligned on the mandrel 16 such that the helical channel 17 in the surface of the mandrel 16 terminates at the inner base 5 of the second end 4 of the blank vascular graft 12. In some embodiments, a visible line (not shown) is pre-printed onto the outer surface of the blank vascular graft 12, extending parallel to the longitudinal axis of the tubular portion 13. The visible line enables the blank vascular graft 12 to be fitted on the mandrel 16 and aligned without twisting of the tubular portion 13. The blank vascular graft 12 is partially pushed into the helical channel 17 in the surface of the mandrel 16. This can be carried out using a spatula.

The mandrel 16, with the blank vascular graft 12 on it is then placed within the two semi-circular channels 21, 22 in the mould blocks 19, 20 such that the injection hole formed by the helical channels 26, 27 is aligned with the helical channel 17 in the surface of the mandrel 16. Because the blank vascular graft 12 has been partly pushed into the helical channel 17 in the surface of the mandrel 16, it is possible to ensure this alignment visually. In addition, the mandrel 16, together with the blank vascular graft 12 are aligned such that the successive turns of the pre-formed external support helix 19 are aligned with and are in the same phase as the helical channel formed by the arcuate grooves 25 in the mould blocks 19, 20. In particular, the helical channel formed by the arcuate grooves 25 overlaps slightly with (or alternatively abuts) the preformed external support helix 29 but continues on in the direction of the second end 4 of the blank tubular graft 12, beyond the pre-formed termination point 14. The two mould blocks 19, 20 are then held tight together, for example by retaining screws.

It is to be appreciated that the mandrel 16, the cylindrical bore formed by the semi-circular channels 21, 22 and the blank vascular grafts 12 are sized such that the blank vascular graft 12 is tightly sandwiched between the two mould blocks 19, 20 and the mandrel 16.

The mould 15, together with the blank vascular graft 12, are then placed in a pressurised bore injection moulding machine. In this embodiment, the pressure is raised to 100 PSI (639 kPa) but the optimum of pressure to be used in each embodiment is dependent on the materials used.

Molten polyurethane is injected via the injection hole formed by the injection channels 26, 27 into the interior of the mould 16. The molten polyurethane deforms the blank vascular graft 12 by pressing it into the helical channel 17 in the mandrel 16 to create a helical groove in the outside surface of the vascular graft 1 into which the molten polyurethane flows thus forming the deformation helix 11. This simultaneously creates the corresponding internal inducer helix 10 (see FIGS. 1 to 4) on the inside surface of the vascular graft 1.

The molten polyurethane also flows along the helical channel formed by the arcuate grooves 25 in the mould blocks 19, 20. Thus only a single injection of molten polyurethane is required to fill both the helical groove in the outer surface of the vascular graft 1 and the helical channel in the mould blocks 19, 20.

The molten polyurethane that fills the helical channel in the mould blocks 19, 20 effectively extends the pre-formed external support helix 29 beyond the pre-formed termination point 14, in the direction of the second end 4 of the blank vascular graft 12 for an additional two successive revolutions such that there is a contiguous external support helix 7. The heat and pressure sinters the polyurethane onto the ePTFE vascular graft 12. The mould 15 is then opened and the finished vascular graft 1 removed from the mandrel 16 and allowed to cool. Where the additional successive turns of the external support helix 7 intersect with the deformation helix 11, the two helices are fused as a single polyurethane component and thus the deformation helix 11 is held in place at its initiation point 9.

It has been found that when using polyurethane to form the deformation and support helices 11, 7 and ePTFE to form the tubular portion 2, the combination of 100 PSI (689 kPa) moulding pressure, and 190° C. operating temperature provides an optimum combination for the sintering step. In particular, the tubular portion 2 is not excessively deformed and molten polyurethane flow is maximised, bringing the moulding time to the minimum of 5 seconds. Consequently, the vascular graft 1 is finished with the two polyurethane helices 7, 11 formed on it quickly and easily.

In order to be used, the finished vascular graft 1 is implanted into a patient, usually by a surgeon, as is known in the art. Such grafts can be implanted in procedures including, but not limited to the following: an above knee femoropopliteal bypass; a below knee femoropopliteal bypass; as vascular dialysis access grafts across the elbow; as axillofemoral grafts; as aortobifemoral grafts across the hip; and as femorodistal grafts to the mid-calf or below/across the knee of a patient.

In brief, an aperture is formed in a healthy section of blood vessel, adjacent to a damaged section of blood vessel which is to be bypassed. The aperture is "egg-shaped" being of corresponding shape to the orifice defined by the second end 4 of the vascular graft 1, except slightly smaller. The second end 4 of the vascular graft is located over the aperture formed in the blood vessel and then the surgeon sutures the vascular graft 1 to the healthy section of blood vessel, joining the edge of the second end 4 of the vascular graft 1 to the edge of the aperture in the blood vessel. The egg shape of the orifice defined by the second end 4 of the vascular graft 1 provides a surgeon with a maximum amount of material in order to carry out the suturing step which assists the surgeon in performing the procedure. It is particularly helpful for the surgeon to have this additional material when suturing around the inner base 5 of the second end 4 of the vascular graft 1. The relative flexibility of the second region of the vascular graft 1 allows a surgeon to suture the vascular graft 1 to the blood vessel more easily. Furthermore, because the internal inducer helix 10 terminates at the second end 4 of the tubular portion 2, within 90° either side of the inner base 5, the surgeon has some leeway in positioning of the graft. More specifically, even if the alignment of the graft is off-centre with respect to the healthy blood vessel, or the angle of approach of the vascular graft is relatively high, the helical flow of blood imparted by the internal inducer helix 10 is still maintained.

The first end 3 of the vascular graft 1 is also sutured to another section of healthy blood vessel, so that the vascular graft 1 bypasses the damaged section of blood vessel. The process of attachment of the first end 3 may correspond to that of the second end 4. In embodiments where a visible line has been pre-printed on the tubular portion 2, the surgeon may refer to the visible line to ensure that the vascular graft does not become twisted during the implantation procedure.

While the procedure is taking place, any blood is prevented from passing through the blood vessel being operated on but once the suturing of vascular graft 1 to the blood vessel is complete, blood is allowed to pass through the blood vessel and into the vascular graft 1, from the first end 3 to the second end 4. As the blood passes the internal inducer helix 10, helical flow is imparted on the blood and this helical flow continues as the blood passes out of the second end 4 of the vascular graft 1 and into the healthy blood vessel. The helical flow of blood reduces turbulence at the junction between the vascular graft 1 and the blood vessel, minimising cell damage and plaque build up. The damaged section of the blood vessel is usually occluded and totally incorporated into the surrounding tissue, but occasionally it is removed.

It has unexpectedly been found that such a vascular graft 1 balances the requirement for flexibility of the graft during implantation and stiffness of the graft when implanted (to avoid kinking) both at sites which do not cross a joint of a patient (e.g. an above-knee femoropopliteal bypass) and at sites which do cross a joint of the patient (e.g. a below-knee femoropopliteal bypass; vascular access grafts across the elbow; aortobifemoral grafts across the hip and femorodistal grafts to the mid-calf or below/across the knee of the patient).

In preferred embodiments of the present invention, a carbon coating is applied to the interior surface of the tubular portion 2. The advantage of adding the coating is that it enhances the biocompatibility and tissue response of the vascular graft 1. Processes for carbon coating inside the vascular graft 1 are known in the art.

The size of the vascular graft 1 is dependent upon the blood vessel which is it is intended to replace. Typically, the diameter of the vascular graft is between 4 mm and 12 mm when replacing a peripheral blood vessel and between 18 mm and 40 mm when replacing a non-peripheral blood vessel. Vascular grafts outside these ranges of diameter are nevertheless within the scope of the present invention. Where the vascular graft 1 is to be implanted between the groin and just above the knee of a patient, a diameter of 8 mm is particularly preferred.

In the above-described embodiments, the vascular graft 1 is made from ePTFE and the external support helix 7 and the deformation helix 11 are made from polyurethane. However, in other embodiments of the invention, different materials are selected in order to take advantage of particular properties of those materials. For example, instead of using polyurethane, another moulding material such polyester or PTFE, that can be injected in liquid form and then solidified is used in some embodiments.

Similarly, in some embodiments the tubular portion 2 is made from a fabric such as a knitted, woven or extruded polymer. In some embodiments, the tubular portion 2 and the moulding material consists of the same, or similar materials such as ePTFE and PTFE, respectively, or both consisting of polyurethane. What is important is that the injected moulding material should have a melting temperature lower than the melting temperature of the material from which the tubular portion 2 is made.

It is to be appreciated that in the above described embodiments of the invention the conditions of 689 kPa and 190° C. are referred to merely as the optimum conditions when the vascular graft 1 is made from ePTFE and polyurethane is injected to form the deformation helix 11 and the continuation of the external support helix 7 and with the mould 15 as described. However, the optimum conditions will be different in alternative embodiments. In particular, the optimum conditions are dependent on the mould conditions and on the material from which the tubular portion 2 is made and on the injected moulding material used. Nevertheless, a generally preferred range of conditions is from 600 to 800 kPa and from 170° to 210° C.

In some alternative embodiments, the vascular graft 1 is provided with more than one deformation helix 11 and corresponding internal inducer helix 10 and/or more than one external support helix 7. In these embodiments, it is preferred that the multiple helices be equally spaced about the circumference of the vascular graft 1.

While the above embodiments of the present invention have been described in relation to vascular grafts, in other embodiments of the invention different tubular conduits are provided. For example, in some embodiments of the invention, the tubular portion 2 is a non-vascular graft. The tubular portion 2 need not be a precisely circular cross-section, although that is most preferred, but the cross-section should preferably be such as to avoid excess turbulence in the flow of fluid passing through it.

What is claimed is:

1. A tubular conduit comprising:
    a flexible tubular portion made from a flexible material and being of unitary construction, the tubular portion having an exterior, an interior, and an axis;
    an external helical formation extending around the exterior of, and parallel to the axis of, the tubular portion and defining a first region of the tubular portion, the external helical formation being for supporting the tubular portion; and
    an internal helical formation, protruding inwardly of the interior of the tubular portion and extending parallel to the axis of the tubular portion and defining a second region of the tubular portion, the internal helical formation being for imparting helical flow on fluid passing through the tubular portion,
    wherein the first region does not overlap completely with the second region.

2. The tubular conduit according to claim 1 wherein the first and second regions overlap.

3. The tubular conduit according to claim 2 wherein the overlap between the first and second regions is of a length of between 1 and 5 revolutions of the external helical formation.

4. The tubular conduit according to claim 3 wherein the overlap between the first and the second regions is of a length of two revolutions of the external helical formation.

5. The tubular conduit according to claim 1 wherein the tubular portion comprises one end and the internal helical formation terminates at said one end of the tubular portion.

6. The tubular conduit according to claim 5, wherein said one end of the tubular portion tapers from an inner base to an outer tip and said one end of the tubular portion defines a substantially elliptical orifice.

7. The tubular conduit according to claim 1 wherein the first region does not extend throughout all parts of the second region that extend along sections of the tubular portion having a complete perimeter.

8. A method of making a tubular conduit according to claim 1, the method comprising the steps of:
    (i) providing a flexible tubular portion having an exterior, an interior, an axis, and a pre-formed helical formation extending axially along the exterior of a region of the tubular portion;
    (ii)(a) flowing a moulding liquid in a first axially extending, helical form around the exterior of the tubular portion, the first helical form having the same helix angle and phase as the pre-formed helical formation and extending beyond one end of the pre-formed helical formation such that a contiguous external helical formation is formed,
    (ii)(b) deforming the tubular portion so as to provide an internal helical protrusion on the inside of the tubular portion and a corresponding external helical groove, and
    (ii)(c) flowing the moulding liquid into the external helical groove to form a second axially extending helical form around the exterior of the tubular portion; and
    (iii) solidifying the moulding liquid,
    wherein the contiguous external helical formation defines a first region of the tubular portion and the second helical form defines a second region of the tubular portion and the first region does not overlap completely with the second region.

9. The method according to claim 8, wherein step (ii) comprises locating the tubular portion over a mandrel; and encasing the tubular portion within a mould such that the tubular portion is sandwiched between the mandrel and the mould.

10. The method according to claim 9, wherein the mould has an axially extending helical channel about its inside surface and step (b) further comprises the step of introducing the moulding liquid between the tubular portion and the mould such that the moulding liquid flows into the helical channel in the mould.

11. The method according to claim 10, wherein the tubular portion is aligned within the mould such that the pre-formed helical formation is in the same phase as and overlaps with or abuts the axially extending helical channel about the inside surface of the mould.

12. The method according to claim 9, wherein the mandrel has an axially extending helical channel on its surface and wherein step (a) further comprises the step of introducing the moulding liquid between the tubular portion and the mould such that the moulding liquid deforms the tubular portion by pressing the tubular portion into the helical channel on the mandrel to provide the internal helical protrusion.

13. The method according to claim 12 wherein one end of the tubular portion tapers from an inner base to an outer tip such that said one end defines an orifice which is substantially elliptical.

14. The method according to claim 8 wherein, the first region and the second region overlap.

15. The method according to claim 14, wherein the overlap between the first and second regions is of a length of between 1 and 5 revolutions of the contiguous external helical formation.

16. The method according to claim 8 wherein the first region does not extend throughout all parts of the second region that extend along sections of the tubular portion having a complete perimeter.

17. The method according to claim 15 herein the overlap between the first and second regions is of a length of two revolutions of the contiguous external helical formation.

* * * * *